United States Patent [19]
O'Neill et al.

[11] Patent Number: 5,891,033
[45] Date of Patent: *Apr. 6, 1999

[54] SYSTEM FOR RADIOLOGICALLY SCANNING THE SPINE FOR MEASURING BONE DENSITY

[75] Inventors: William O'Neill, Ann Arbor, Mich.; James R. Warne, Washington, Pa.

[73] Assignee: Hologic, Inc., Waltham, Mass.

[*] Notice: The term of this patent shall not extend beyond the expiration date of Pat. No. 5,986,273.

[21] Appl. No.: 455,188

[22] Filed: May 31, 1995

(Under 37 CFR 1.47)

Related U.S. Application Data

[63] Continuation of Ser. No. 295,171, Aug. 22, 1994, Pat. No. 5,572,998, which is a continuation of Ser. No. 947,247, Sep. 18, 1992, abandoned, which is a continuation-in-part of Ser. No. 360,347, Jun. 5, 1989, Pat. No. 5,165,410, which is a continuation-in-part of Ser. No. 204,513, Jun. 9, 1988, abandoned, which is a continuation-in-part of Ser. No. 50,726, May 15, 1987, abandoned.

[51] Int. Cl.$^6$ ........................................... A61B 5/00
[52] U.S. Cl. ........................... 600/425; 378/55; 378/197
[58] Field of Search ................... 128/653.1, 659; 378/54–56, 119, 146, 193, 195–198; 600/425, 436, 407

[56] References Cited

U.S. PATENT DOCUMENTS

| | | | |
|---|---|---|---|
| 3,803,417 | 4/1974 | Kok | 250/447 |
| 3,944,830 | 3/1976 | Dissing | 250/358 |
| 3,988,585 | 10/1976 | O'Neill et al. | 250/363 |
| 4,012,636 | 3/1977 | Engdahl et al. | 250/363 |
| 4,107,532 | 8/1978 | MaCovski | 250/360 |
| 4,144,457 | 3/1979 | Albert | 250/445 |
| 4,275,305 | 6/1981 | Racz et al. | 250/445 |
| 4,342,916 | 8/1982 | Jatteau et al. | 378/4 |
| 4,358,856 | 11/1982 | Steivender et al. | 378/167 |
| 4,365,343 | 12/1982 | Grady et al. | 378/181 |
| 4,495,645 | 1/1985 | Ohhashi | 382/6 |
| 4,590,378 | 5/1986 | Platz | 250/363 |
| 4,618,133 | 10/1986 | Siczek | 269/323 |
| 4,649,560 | 3/1987 | Grady et al. | 378/196 |
| 4,653,083 | 3/1987 | Rossi | 378/196 |
| 4,716,581 | 12/1987 | Barud | 378/198 |
| 4,829,549 | 5/1989 | Vogel et al. | 378/55 |
| 4,856,044 | 8/1989 | Tanguy et al. | 378/193 |
| 4,947,414 | 8/1990 | Stein | 378/55 |
| 4,986,273 | 1/1991 | O'Neill et al. | 128/653 |
| 5,165,410 | 11/1992 | Warne et al. | 128/653 |
| 5,572,998 | 11/1996 | O'Neill et al. | 128/653.1 |

FOREIGN PATENT DOCUMENTS

| | | |
|---|---|---|
| 0 253 742 | 7/1987 | European Pat. Off. . |
| 0 265 302 | 9/1987 | European Pat. Off. . |
| 2 238 706 | 2/1974 | Germany . |
| P 24 12 161.7 | 3/1974 | Germany . |
| 86/07531 | 12/1986 | WIPO . |
| 90/10859 | 9/1990 | WIPO . |

OTHER PUBLICATIONS

Rutt, B.K., et al., "High Speed, High–Precision Dual Photon Absorptiometry", Reprint of pester exhibited at meeting at the American Society of Bone and Mineral Research, Jun. 16, 1985, Washington, D.C.

Pearce, R.B., "DPA Gaining Strength in Bone Scanning Debate", *Diagnostic Imaging* (Jun. 1986).

Norland Corporation advertising brochure for OsteoStatus System pp. 1–8.

(List continued on next page.)

*Primary Examiner*—Ruth S. Smith
*Attorney, Agent, or Firm*—Hamilton, Brook, Smith & Reynolds, PC

[57] ABSTRACT

An apparatus employing radiation for measuring bone density in which the bone can be scanned from different angles. The multidirectional scanning is accomplished by rotating the radiation source and detector about the stationary object being irradiated.

19 Claims, 2 Drawing Sheets

OTHER PUBLICATIONS

A New Dimension in Dual–Photon Absorptiometry Novo Introduces the BMC–Lab 23, Light Years Ahead.

Lunar Radiation Corporation's Users Manual for Lunar DP3 Dual Photon Scanner.

Brochure, "Osteotek Bone Densitometry", Medical & Scientific Enterprises, Inc.

Sartoris, D.J. et al., "Trabecular Bone Denisty in the Proximal Femur: Quantitative CT Assessment", *Radiology*, 160:707–712 (1986).

Mazess, R.B., et al., "Spine and Femur Density Using Dual–Photon Absorptiometry in US White Women", *Bone and Mineral*, 2:211–219 (1987).

Weissberger, M.A., et al., "Computed Tomography Scanning for the Measurement of Bone Mineral in the Human Spine", *Journal of Computer Assisted Tomography*, 2:253–262 (Jul. 1978).

Genant, H., "Asssessing Osteoporosis: CT's Quantitative Advantage", *Diagnostic Imaging*, (Aug. 1985).

Wahner et al. "Assement of Bone Mineral. Part 1" *J. Nuclear Medicine* 25(10):1134–1141 (1984).

Mazess, "Dual Photon Absorptiometry and Osteoporosis—Absorptiometric Instrumentation" Meeting publication.

SYSTEM FOR RADIOLOGICALLY SCANNING THE SPINE FOR MEASURING BONE DENSITY

RELATED APPLICATIONS

This application is a Continuation of U.S. Ser. No. 08/295,171 filed Aug. 22, 1994 (now U.S. Pat. No. 5,572,998) which is a File Wrapper Continuation of U.S. Ser. No. 07/947,247 filed Sep. 18, 1992 (now abandoned) which is a Continuation-in-Part of U.S. Ser. No. 07/360,347 filed Jun. 5, 1989, now U.S. Pat. No. 5,165,410, which is a continuation-in-part of U.S. Ser. No. 07/204,513 filed Jun. 9, 1988 (now abandoned) which is a Continuation-in-Part of U.S. Ser. No. 07/050,726 filed May 15, 1987 (now abandoned).

BACKGROUND OF THE INVENTION

This invention relates to radiologic measuring devices, and more particularly, to the use of radiation in measuring bone structure.

The diagnostic use of radiation in evaluating bone structure has recently been applied in assessing bone demineralization that occurs with advancing age. Bone mineral is lost from all parts of the skeleton, and at a linear rate from the lumbar spine, starting at about 35 years of age. The resultant demineralization results in a high risk of fractures with an increased associated mortality and morbidity. In evaluation of the spine, there is a very good correlation between dual photon densitometry measurements of bone density and fracture resistance in excised vertebrae subjected to compression testing. It is also important to evaluate mineral loss in the hip, as appendicular losses often match or exceed spine loss in patients over 70.

Dual photon absorptiometry enables non-invasive quantitative analysis of bone mineral in regions of the body that were previously inaccessible using single photon absorptiometry. The use of two photon energies minimizes errors that result from irregular body contour and soft tissue inhomogeneities. Essentially, two photon energies are necessary to allow discrimination of two substances of a given system. In this case between bone mineral and soft tissue. The most commonly used photon energies in dual photon scanning are 44 and 100 KeV. The measurements of the attenuation of this radiation as it passes through the body yields the bone mineral density.

SUMMARY OF THE INVENTION

The present invention involves the multidirectional measurement of human bone densities for diagnostic purposes. A radiation source, and a detector used for measuring the radiation transmitted through the object being measured, are rigidly aligned by a bracket or arm. This detector is mounted in a telescoping mechanism to permit control over the source/detector distance. The arm and the attached source and detector, are mounted on an "x-y" table that permits scanning of objects over a predetermined planar area. This apparatus is mounted so that the source, detector, and scanning mechanism can be rotated to view a stationary object from different angles.

In a preferred embodiment of the invention, the pivot axis about which the arm rotates is displaceable so that the source will clear the table upon rotation. The rotating apparatus may be mounted in a drawer with guides or rails that telescope out to support the system during rotation. The rotating elements are weighted so that very little pressure is necessary to rotate the system. The weight is distributed so that if the mechanism is stopped at any point during rotation, it will at most slowly accelerate under its own weight. If the center of gravity of the rotating mechanism is approximately along the pivot axis, this condition will be met. One weight is placed in the detector to vertically adjust the center of gravity. A second weight is placed adjacent the scanning assembly to horizontally adjust the center of gravity.

DETAILED DESCRIPTION OF THE INVENTION

Existing scanner assemblies used in bone densitometry generally permit unidirectional scanning of patients only. To obtain lateral or side views, for example, the patient must be turned. This movement of the patient is often difficult or impossible depending upon their physical condition.

Figure 1:
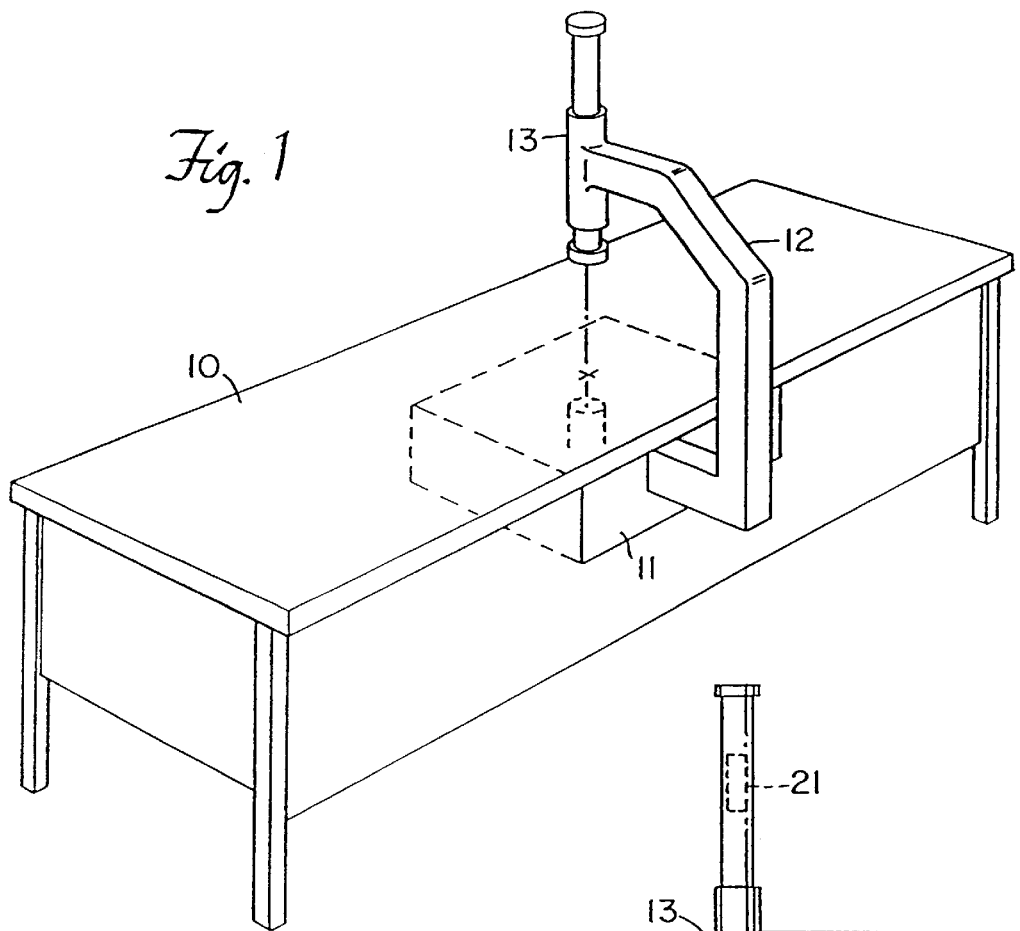
FIG. 1 is a perspective view of the bone densitometer.
Figure 2:
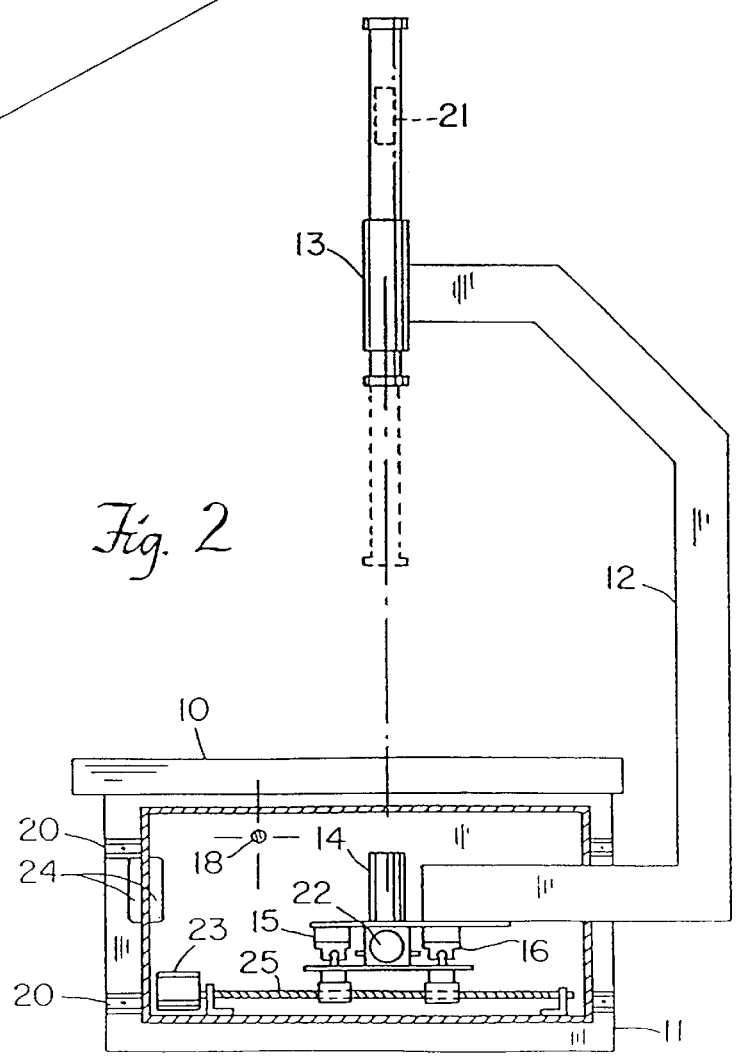
FIG. 2 is a side view of the radiation source and detector in the interior position.

A dual photon bone densitometer used in diagnosing osteoporosis is illustrated generally in FIG. 1. A table 10 on which the patient lies has a drawer assembly 11 which is pulled out from under the table on the side from which a bracket 12 protrudes. The bracket 12 extends in a "C" shape from the drawer assembly 11 to a detecting apparatus 13. FIG. 2 shows, in a cross-sectional view, the relationship between the detector 13 and the contents of the drawer assembly 11.

A radiation source 14 is mounted on a moveable platform 15. The source 14 is rigidly aligned with the detector 13 by bracket 12 to insure that radiation emitted from the source is received by the detector regardless of the angle to which the source-detector axis is rotated. The entire rotatable apparatus is mounted on a tray or "saddle" 17. The saddle 17 is rotatably mounted onto the assembly plates 19. The plates 19 in one embodiment constitute the side walls of a drawer which compactly houses the source and scanning apparatus.

Figure 3:
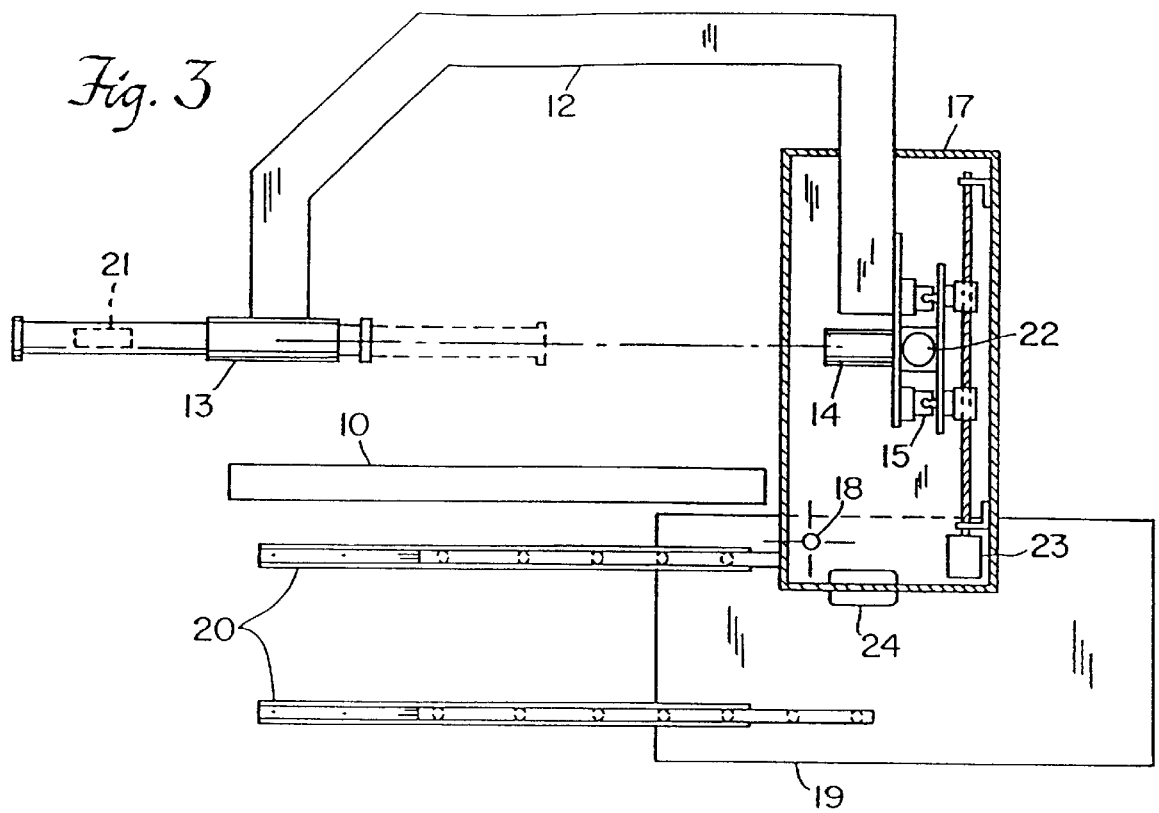
FIG. 3 is a side view of the apparatus rotated to the lateral position.

To rotate the apparatus from the anterior position shown in FIG. 2 to the lateral position shown in FIG. 3, the following steps must be taken. The user releases a locking mechanism and pulls the arm horizontally to one side of the table so that the saddle 17 and plates 19 slide the source from under the center of the table to avoid contact with the table during rotation. In one embodiment of the invention the source is approximately one inch below the table during anterior scanning and thus cannot be rotated without lateral movement. Source proximity to the table is desirable, as the source and detector are preferably as close to one another as possible to yield the best possible image. The drawer assembly plates 19 telescope out along the glides 20 until the pivot point 18 is astride the table 10. The plates 19 are then locked in position by a locking mechanism (not shown). The arm 12 and the attached source and saddle assembly 17 are rotated manually by the user about the axis 18 to the desired position. Note that the pivot axis location must be chosen so that the source and scanning apparatus are rotated into a position just above the plane of the table. This insures that objects positioned on the table can be fully scanned laterally. The pivot location also affects the adjustment of the center of gravity as discussed below. In an alternative embodiment of the invention, the lateral movement of the drawer assembly and/or the rotation may be automatically controlled by adding the necessary motor and control systems.

FIGS. 2 and 3 also illustrate the presence of weights 21 and 24. After initial assembly of the apparatus, the center of gravity of the rotating elements must be adjusted to assure ease of manual rotation. In a preferred embodiment of the invention, the center of gravity of the rotating elements is located along the pivot axis 18. When the center of gravity is so situated the rotating elements will not accelerate under their own weight when the bracket 12 is rotated to any chosen angle, stopped and released.

Figure 4:
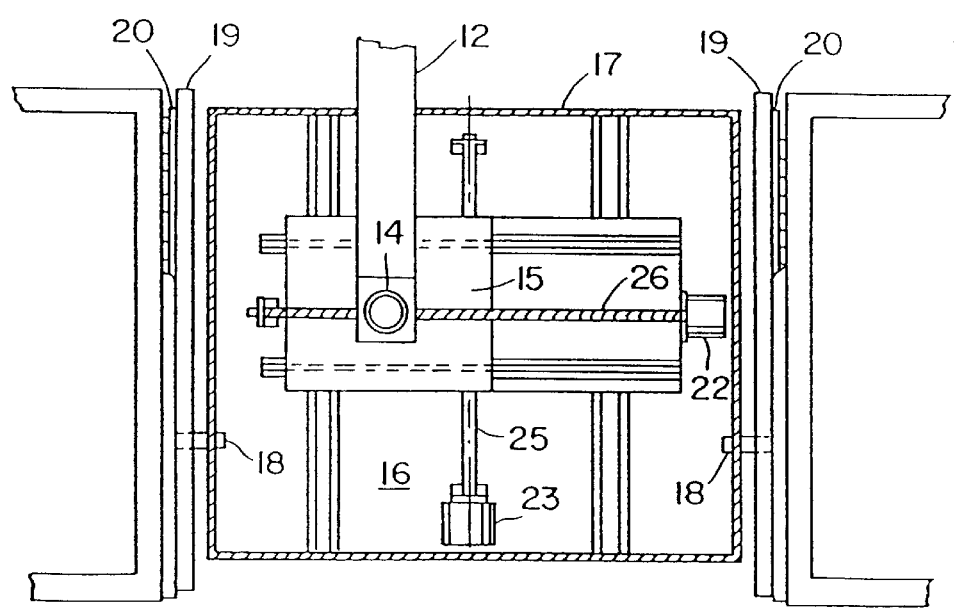
FIG. 4 is a top view of the saddle and drawer assembly.

FIG. 4 shows a top view of the drawer assembly 11 and illustrates the location of the pivot axis 18, the glides 20 for displacement of the plates 19, and the tracks 26 on which the platform 15 rides. The platform 15, as well as the attached source 14, bracket 12, and detector 13, are moved in a plane perpendicular to the source-detector axis. The driving mechanism for the scanning motion is a so-called "x-y" table 16. The scanning mechanism is comprised of threaded bars, one running along the longitudinal or "y" axis 26 of the table, the second 25 running perpendicular to the first across the width or "x" axis of the table. The platform 15 has threaded housings which receive, and are driven by, the two threaded bars. The threaded "x" bar 25 is rotated by a motor 23 and the threaded "y" bar 26 is rotated by the motor 22. When the scanning assembly is rotated along with the source and detector, this insures full scanning capability at any angle. In a preferred embodiment of the invention, the scanning mechanism is controlled automatically feeding by the scanning rate and the size of the area to be scanned into a computer, which then triggers the radiation source and coordinates the desired scan.

During initial rotation of the system from the vertical position, the weight of the saddle and enclosed elements controls the balancing of the bracket 12 and the attached components. The weights 24 are added to the front wall of the saddle to adjust the center of gravity in the horizontal plane. The weight 21 is added to the detector system to adjust the center of gravity in the vertical plane. As the system is rotated through larger angles from the vertical (e.g. 45°–90°), the correct weighting of the bracket and detector by weight 21 becomes more important to maintain ease of manual rotation.

By rotating the detector arm, scanning of the lumbar spine in both the anterior and lateral projections is now possible without repositioning the patient. The patient remaining in the supine position for both the lateral and anterior-posterior projection maintains the correct alignment of both projections, permits direct correlation of the two studies, and anatomically is diagnostically correct.

Performing the lateral image as the first study may enable the physician to observe extra-osseous calcification in tissue overlying the lumbar spine. In the anterior—posterior projections, such extra-osseous calcification cannot be distinguished from bone, and could therefore interfere with accurate bone density measurements in that projection. The bone being studied may be examined in real time by amplifying the signal output from the detector and displaying it on a C-T screen.

While the invention has been particularly shown and described with reference to preferred embodiments thereof, it will be understood by those skilled in the art that various changes in form and details may be made without departing from the spirit and scope of the invention as defined in the appended claims.

We claim:

1. A method of measuring bone density in the spine comprising:

scanning a region of a spinal column at a first angle with a scanning assembly having a radiation source and a detector, the detector being aligned along an alignment axis with the source to receive radiation transmitted at two energies through the region from the source during the scanning of the source and detector along an axis of the spinal column;

rotating the radiation source and detector about a horizontal axis to a second angle such that the source and detector alignment axis extends through the spinal region at an angle different from the first angle;

scanning a region of the spinal column with the scanning assembly to measure radiation from the source that is transmitted through the region to the detector at the second angle;

determining the density of bone within the spinal region from radiation received by the detector during scanning of the region; and forming an image of the region from radiation received by the detector.

2. The method of measuring bone density of claim 1 further comprising correlating the bone density measurement from the first angle with the bone density measurement from the second angle.

3. The method of measuring bone density of claim 1 further comprising determining extra-osseous calcification of bone within the region.

4. The method of measuring bone density of claim 1 wherein each of the scanning steps further comprise displacing the detector in two perpendicular directions in a plane orthogonal to the alignment axis.

5. The method of measuring bone density of claim 1 wherein scanning at the first angle provides an anterior view of the spinal column.

6. The method of measuring bone density of claim 1 further comprising displacing the scanning assembly and the alignment axis to one side of the spinal region before rotating the assembly to the second angle.

7. The method of measuring bone density of claim 6 further comprising displacing the scanner assembly in a drawer such that said scanner assembly is suspended along the horizontal axis within the drawer, and is rotatable about said horizontal axis.

8. The method of measuring bone density of claim 7 wherein said drawer is displaced using telescoping rails in a direction perpendicular to the horizontal axis.

9. The method of measuring bone density of claim 7 further comprising balancing the source and detector with a balance element during rotation.

10. The method of measuring bone density of claim 1 further comprising positioning the object to be scanned on a table.

11. A method of scanning the spine of a patient comprising:

positioning a human patient on a support surface, the spine of the patient extending along an axis of the support surface;

providing a C-shaped member mounted relative to the support surface, the C-shaped member rigidly aligning a radiation source and detector;

scanning a region of a patient's spinal column at a first angle with the C-shaped member, source and detector to detect with the detector radiation at two energies that is transmitted through the region from the source while the C-shaped member is being driven along the axis of the support surface by a motor, the source emitting radiation at said two energies;

determining bone density in the spinal column from radiation detected with the detector at the two energies during the scanning at the first angle;

rotating the C-shaped member, the radiation source and detector about the support surface to a second angle such that the source and detector are aligned through the spinal region at an angle different from the first angle;

scanning a region of the spinal column with the C-shaped member, source and detector, the detector receiving radiation from the source that is transmitted through the region to the detector at the second angle while the C-shaped member is being driven along the axis of the support surface.

12. The method of claim 11 further comprising providing a second motor to drive the C-shaped member in a second direction that is perpendicular to the axis of the support surface and scanning the patient's hip with the source and detector to measure bone density of the hip.

13. The method of claim 11 comprising automatically controlling scanning of the C-shaped member using scan parameters programmed in a computer.

14. The method of claim 11 comprising displacing the C-shaped member to one side of the spinal region after scanning at the first angle and before rotating the C-shaped member to the second angle.

15. A method of scanning a region of a patient's lumbar spine comprising:

positioning a human patient on a support surface, the lumbar spine of the patient extending along an axis of the support surface;

providing a C-shaped member mounted relative to the support surface, the C-shaped member rigidly aligning a radiation source and a detector in a vertical plane and being selectively driven in a first direction along the axis of the support surface by a motor, and selectively causing relative displacement between the support surface and the C-shaped member in a second direction that is perpendicular to the support surface axis;

scanning a region of the patient's lumbar spine at a first angle with the C-shaped member to detect with the detector radiation at two energies that is transmitted in the vertical plane through the region from the source that emits radiation at said two energies, the C-shaped member being driven by the motor to scan along the axis of the support surface;

determining bone density in the lumbar spine from radiation detected with the detector at the two energies during the scanning at the first angle;

rotating the C-shaped member, the radiation source and the detector in the vertical plane about the support surface to a second angle such that the source and detector are aligned laterally through the region of the lumbar spine at an angle different from the first angle;

scanning a region of the lumbar spine with the C-shaped member, source and detector such that the detector detects radiation from the source that is transmitted laterally through the region to the detector while the C-shaped member is being driven in the first direction along the axis of the support surface at the second angle.

16. The method of claim 15 including the step of displacing said C-shaped member laterally relative to said support surface in a direction perpendicular to the axis of the support surface, between said scanning at said first angle and the scanning at the second angle.

17. The method of claim 16 further comprising laterally displacing the C-shaped member with a second motor.

18. The method of claim 16 further comprising providing rails to support the C-shaped member relative to the support surface during lateral displacement of the C-shaped member.

19. A method for radiologically scanning the spine of a patient comprising;

providing a scanning assembly comprising a horizontal support surface upon which the patient can lie in a supine position;

providing a radiation source capable of producing radiation of at least two energies;

providing a detector for detecting radiation emitted from the source;

providing a member of substantially C-shape to which the source and detector are attached to provide rigid alignment of the source and the detector along an alignment axis lying in a vertical plane, said C-shape member and the source and detector thereon, being rotatable about a generally horizontal axis;

providing a drive mechanism for displacing the C-shaped member, source and detector in a direction orthogonal to the vertical plane containing said alignment axis to scan along the spine of the patient at a first angle of the alignment axis, the C-shaped member, source and detector being rotatable about the horizontal axis to a second position such that the alignment axis in said vertical plane extends through the region of the body at a second angle different from the first angle, the drive mechanism capable of displacing the C-shaped member, source and detector in said orthogonal direction to scan along the spine of the patient at the second angle of the alignment axis, positioning the patient to lie in a supine position on the support surface, with said scanning assembly scanning along a region of the patient's spinal column, with said substantially C-shaped member in a first position to receive radiation from the source transmitted along said alignment axis at the first angle through the spinal region of the patient from the source during scanning;

determining bone density in the spinal column from radiation detected with the detector at the two energies during the scanning at the first angle;

rotating the substantially C-shaped member and the attached radiation source and detector about said horizontal axis to a second position such that the source and detector alignment axis extends laterally through the spinal region at the second angle which is different from the first angle;

and scanning along a region of the spinal column with the scanning assembly such that the detector receives radiation from the source that is transmitted through the region to the detector at the second angle;

thereby to provide radiological information concerning the spine, based on said two energies, and based on exposures at said first and second angles while said patient remains in supine position.

* * * * *